United States Patent
Henton et al.

(10) Patent No.: US 9,260,388 B2
(45) Date of Patent: Feb. 16, 2016

(54) PROCESS FOR PREPARING ALKYL PYROGLUTAMIC ACIDS

(71) Applicant: DOW GLOBAL TECHNOLOGIES LLC, Midland, MI (US)

(72) Inventors: Daniel R. Henton, Midland, MI (US); Cynthia L. Rand, Sanford, MI (US); Sze-Sze Ng, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/364,218

(22) PCT Filed: Dec. 13, 2012

(86) PCT No.: PCT/US2012/069528
§ 371 (c)(1),
(2) Date: Jun. 10, 2014

(87) PCT Pub. No.: WO2013/090591
PCT Pub. Date: Jun. 20, 2013

(65) Prior Publication Data
US 2014/0342966 A1    Nov. 20, 2014

Related U.S. Application Data

(60) Provisional application No. 61/576,023, filed on Dec. 15, 2011.

(51) Int. Cl.
| | | |
|---|---|---|
| *C11D 3/28* | (2006.01) | |
| *C07D 207/18* | (2006.01) | |
| *C07D 207/28* | (2006.01) | |
| *C07D 207/02* | (2006.01) | |
| *C11D 1/10* | (2006.01) | |
| *C11D 3/33* | (2006.01) | |
| *A61K 8/49* | (2006.01) | |
| *A61Q 5/02* | (2006.01) | |
| *A61Q 19/10* | (2006.01) | |
| *A61K 8/44* | (2006.01) | |
| *B01F 17/00* | (2006.01) | |

(52) U.S. Cl.
CPC ............ *C07D 207/28* (2013.01); *A61K 8/44* (2013.01); *A61K 8/4913* (2013.01); *A61Q 5/02* (2013.01); *A61Q 19/10* (2013.01); *B01F 17/0042* (2013.01); *C07D 207/02* (2013.01); *C07D 207/18* (2013.01); *C11D 1/10* (2013.01); *C11D 3/28* (2013.01); *C11D 3/33* (2013.01); *A61K 2800/49* (2013.01)

(58) Field of Classification Search
CPC ....... C11D 3/28; C07D 207/02; C07D 207/18
USPC .......... 548/532; 546/278.4; 510/500
See application file for complete search history.

(56) References Cited

U.S. PATENT DOCUMENTS

2007/0221215 A1  9/2007  Sugita et al.
2009/0163555 A1*  6/2009  Ivarez Builla Gomez ............... C07D 401/06
                                                        514/343

FOREIGN PATENT DOCUMENTS

| EP | 1 002 525 A2 | 5/2000 |
| EP | 1 980 237 A1 | 10/2008 |
| FR | 2 931 065 A1 | 11/2009 |
| WO | 03/103604 A2 | 12/2003 |
| WO | 2009/074518 A1 | 6/2009 |

OTHER PUBLICATIONS

English Language Machine Translation of FR 2931065.*
Database WPI Week 200965, Thomson Scientific, London, GB: AN 2009-N93697 XP-002694101, (Sep. 2009).
Aoyagi et al., "Constituents of a Cationic Peptide-rich Fraction of Lentinus edodes" Agricultural and Biological Chemistry (1982), vol. 46(4), pp. 987-991.
Fushiya et al., "A new acidic amino acid from a basidiomycetes, lactarius piperatus" Chemical & Pharmaceutical Bulletin (1988), vol. 36(4), pp. 1366-1370.
The International Search Report for PCT/US2012/069528 dated Mar. 19, 2013.
Database Caplus [online] Chemical Abstracts Service, Uenuma, Mikiko et al, "Skin preparation, parakeratosis inhibitors or skin pore shrinking agents, and rough skin treatment agents containing pyroglutamic acid derivatives" XP-002694102, (Sep. 2009).
Database WPI, Thomson Scientific, London, GB: AN 2004-352668 XP-002694103, (Apr. 2004).
The International Preliminary Report on Patentability dated Jun. 17, 2014.

* cited by examiner

*Primary Examiner* — Gregory R Delcotto
(74) *Attorney, Agent, or Firm* — McDonnell Boehnen Hulbert & Berghoff

(57) ABSTRACT

Disclosed are compounds of formulae (I) and (II) and salts, hydrates, or solvates thereof, where $R_1$, $R_2$, $R_3$, $R_5$, and $R_6$ are defined herein, compositions containing these compounds, methods of preparing these compounds, and methods of using these compounds in a variety of applications, such as a surfactant or additive in personal care products.

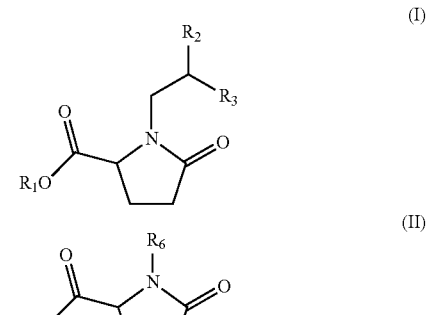

14 Claims, No Drawings

PROCESS FOR PREPARING ALKYL PYROGLUTAMIC ACIDS

CROSS-REFERENCE TO RELATED APPLICATIONS

This application is a U.S. national phase of International Application No. PCT/US2012/069528, filed Dec. 13, 2012, which claims priority from U.S. Provisional Application No. 61/576,023, filed Dec. 15, 2011; the disclosures of both of these applications are incorporated herein by reference in their entireties.

BACKGROUND OF THE INVENTION

1. Field of the Invention

This disclosure relates to compounds and compositions suitable for use in surfactants. In particular, the disclosure relates to alkyl pyroglutamic acid compounds.

2. Description of Related Art

The large shift towards environmentally friendly surfactants has resulted in the need for the industry to provide readily biodegradable and non-toxic surfactants and additives. Surfactants and additives with renewable content can be preferable to their synthetic counterparts with demand being driven by life sustainability initiatives, preferred buying programs and consumer trends.

Alcohol ethoxy sulfates (AES) is a class of anionic surfactant commonly used in personal care shampoo formulation. The trace byproduct from the manufacturing processes of AES (alkoxylation and sulfation), and the skin irritancy associated with AES are not desirable in personal care applications. An ethylene oxide-free (EO-free) and sulfate-free surfactant that is non-irritating is much more preferable in personal care.

Common EO-free and sulfate-free surfactant personal care surfactants are fatty acid soaps, betaines, alpha olefin sulfonates, sulfosuccinates, esters, alkyl polyglucosides, fatty acyl amino acids, fatty amine oxides, and quaternaries. Two common commercially available amino acid surfactants are acyl glutamate and acyl sarcosinate. Acyl glutamate is derived from natural fatty acids and natural glutamic acid, while acyl sarcosinate is derived from natural fatty acids and synthetic glycine. In either case, these amino acid surfactants are commonly accepted as non-toxic and mild. They are used mainly in personal care applications, but not as widely used as alkyl polyglucosides (APG) due, at least in part, to the use of fatty acid chlorides as intermediates in amide formation with the amino acid of choice.

The preparation and use of corrosive acid chlorides imparts cost to the amide-based amino acid surfactants and generation of a full equivalent of waste from the chlorinating reagent. Additionally, the isolation of the desired fatty acid amide from salt byproduct and water also adds cost relative to other surfactants.

SUMMARY OF THE INVENTION

In a broad aspect, the disclosure provides compounds or mixtures thereof, and formulations containing said compounds that are N-alkylpyroglutamic acids, which may be derived from glutamic acid and aldehydes. The properties and composition of the N-alkylpyroglutamic acid derivatives are very dependent on the features of the aldehyde, and the method of production which controls the composition of these glutamic acid derivatives.

Thus, one aspect of the disclosure (embodiment 1) provides compounds of formula (I):

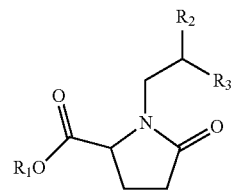

or acceptable salts, hydrates, or solvates thereof; wherein $R_1$ is hydrogen, $C_1$-$C_6$ alkyl, $C_1$-$C_6$ hydroxyalkyl, W, or a polyoxyalkylene moiety having oxyalkyl groups that are the same or different, and where the polyoxyalkylene moiety is capped or uncapped;

where $M^+$ is a cation forming a salt;

$R_2$ and $R_3$ are independently $C_2$-$C_{24}$ alkyl, $C_2$-$C_{24}$ alkenyl, or $C_2$-$C_{24}$ alkynyl, each optionally substituted with one or more of $R_4$; and wherein $R_4$ is halogen, —CN, $C_1$-$C_6$ alkyl, $C_2$-$C_6$ alkenyl, $C_2$-$C_6$ alkynyl, $C_1$-$C_6$ haloalkyl, —NH($C_1$-$C_6$ alkyl), —N($C_1$-$C_6$ alkyl)$_2$, —OH, $C_1$-$C_6$ alkoxy, $C_1$-$C_6$ haloalkoxy, —$CO_2H$, —$CO_2$($C_1$-$C_6$ alkyl), —CON($C_1$-$C_6$ alkyl), —CON($C_1$-$C_6$ alkyl)$_2$, $C_3$-$C_8$ cycoalkyl, aryl, heteroaryl, or heterocyclyl, wherein each cycloalkyl, aryl, heteroaryl, and heterocyclyl are optionally substituted with one or more of halogen, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —$CO_2H$, —$CO_2$($C_1$-$C_6$ alkyl), —CON($C_1$-$C_6$ alkyl), or —CON($C_1$-$C_6$ alkyl)$_2$;

or $R_4$ is polyoxyalkylene moiety having oxyalkyl groups that are the same or different, and where the polyoxyalkylene moiety is capped or uncapped.

The disclosure also provides compositions comprising a compound of formula (I) or mixtures thereof, and at least one additive, excipient or diluent.

Another aspect of the disclosure (embodiment 2) provides compositions comprising at least two compounds selected from the compounds of formula (II):

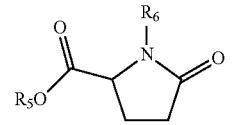

or acceptable salts, hydrates, or solvates thereof; wherein $R_5$ is hydrogen, $C_1$-$C_6$ alkyl, $C_1$-$C_6$ hydroxyalkyl, $M^+$, or a polyoxyalkylene moiety having oxyalkyl groups that are the same or different, and where the polyoxyalkylene moiety is capped or uncapped;

where $M^+$ is a cation forming a salt;

$R_6$ is unbranched or branched $C_2$-$C_{24}$ alkyl, unbranched or branched $C_2$-$C_{24}$ alkenyl, unbranched or branched $C_2$-$C_{24}$ alkynyl, $C_3$-$C_8$ cycloalkyl, or $C_3$-$C_8$ cycloalkyl ($C_1$-$C_6$ alkyl), each optionally substituted with one or more of $R_7$; and wherein $R_7$ is halogen, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —$CO_2H$, —$CO_2$($C_1$-$C_6$ alkyl), —CON($C_1$-$C_6$ alkyl), —CON($C_1$-$C_6$ alkyl)$_2$, $C_3$-$C_8$ cycloalkyl, aryl, heteroaryl, or heterocyclyl, wherein each cycloalkyl, aryl, heteroaryl, and heterocyclyl are optionally substituted with one or more of halogen, —CN, $C_1$-$C_6$ alkyl, $C_1$-$C_6$ haloalkyl, —$NH_2$, —NH($C_1$-$C_6$ alkyl), —N($C_1$-$C_6$ alkyl)$_2$, —OH, $C_1$-$C_6$ alkoxy, $C_1$-$C_6$ haloalkoxy, —$CO_2H$, —$CO_2$($C_1$-$C_6$ alkyl), —CON($C_1$-$C_6$ alkyl), or —CON($C_1$-$C_6$ alkyl)$_2$; and of formula (III):

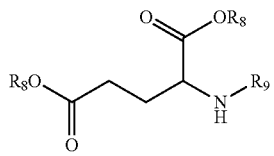

(III)

or acceptable salts, hydrates, or solvates thereof; wherein
each $R_8$ is independently hydrogen, $C_1$-$C_6$ alkyl, $C_1$-$C_6$ hydroxyalkyl, $M^+$, or a polyoxyalkylene moiety having oxyalkyl groups that are the same or different, and where the polyoxyalkylene moiety is capped or uncapped;
where $M^+$ is a cation forming a salt;
$R_9$ is unbranched or branched $C_2$-$C_{24}$ alkyl, unbranched or branched $C_2$-$C_{24}$ alkenyl, unbranched or branched $C_2$-$C_{24}$ alkynyl, $C_3$-$C_8$ cycloalkyl, or $C_3$-$C_8$ cycloalkyl ($C_1$-$C_6$ alkyl), each optionally substituted with one or more of $R_{10}$; and
wherein $R_{10}$ is halogen, —CN, $C_1$-$C_6$ alkyl, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, —$CO_2H$, —$CO_2(C_1$-$C_6$ alkyl), —$CON(C_1$-$C_6$ alkyl), —$CON(C_1$-$C_6$ alkyl)$_2$, $C_3$-$C_8$ cycloalkyl, aryl, heteroaryl, or heterocyclyl, wherein each cycloalkyl, aryl, heteroaryl, and heterocyclyl are optionally substituted with one or more of halogen, —CN, $C_1$-$C_6$ alkyl, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, —$CO_2H$, —$CO_2(C_1$-$C_6$ alkyl), —$CON(C_1$-$C_6$ alkyl), or —$CON(C_1$-$C_6$ alkyl)$_2$.

The disclosure also provides methods of preparing compounds of the disclosure and the intermediates used in those methods. In particular, the disclosure provides a method for preparing a compound of formula (IV) or a mixture of one or more compounds of formula (IV), (embodiment 3):

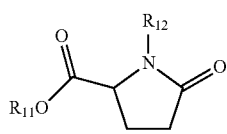

(IV)

or acceptable salts, hydrates, or solvates thereof; wherein
$R_{11}$ is hydrogen, $C_1$-$C_6$ alkyl, $C_1$-$C_6$ hydroxyalkyl, $M^+$, or a polyoxyalkylene moiety having oxyalkyl groups that are the same or different, and can be capped or uncapped; where $M^+$ is a cation forming a salt;
$R_{12}$ is unbranched or branched $C_3$-$C_{24}$ alkyl, unbranched or branched $C_3$-$C_{24}$ alkenyl, or unbranched or branched $C_3$-$C_{24}$ alkynyl, each optionally substituted with one or more of $R_{15}$; and
wherein $R_{15}$ is halogen, —CN, $C_1$-$C_6$ alkyl, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, —$CO_2H$, —$CO_2(C_1$-$C_6$ alkyl), —$CON(C_1$-$C_6$ alkyl), —$CON(C_1$-$C_6$ alkyl)$_2$, $C_3$-$C_8$ cycloalkyl, aryl, heteroaryl, or heterocyclyl, wherein each cycloalkyl, aryl, heteroaryl, and heterocyclyl are optionally substituted with one or more of halogen, —CN, $C_1$-$C_6$ alkyl, $C_1$-$C_6$ haloalkyl, —$NH_2$, —$NH(C_1$-$C_6$ alkyl), —$N(C_1$-$C_6$ alkyl)$_2$, —OH, $C_1$-$C_6$ alkoxy, $C_1$-$C_6$ haloalkoxy, —$CO_2H$, —$CO_2(C_1$-$C_6$ alkyl), —$CON(C_1$-$C_6$ alkyl), or —$CON(C_1$-$C_6$ alkyl)$_2$;

comprising
treating a glutamate of formula:

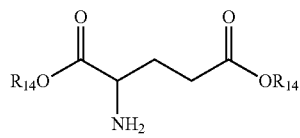

wherein each $R_{14}$ is independently selected form hydrogen, W, $C_1$-$C_6$ alkyl, $C_1$-$C_6$ hydroxyalkyl, —($C_1$-$C_6$ alkyl-O)$_{1-4}$H, aryl, aryl($C_1$-$C_6$ alkyl), or polyoxyalkylene unit;
with an aldehyde of formula:

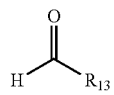

wherein $R_{13}$ is $C_1$-$C_{23}$ alkyl, $C_2$-$C_{23}$ alkenyl, or $C_2$-$C_{23}$ alkynyl, each optionally substituted with one or more of $R_{15}$.

The disclosure also provides intermediates that are useful in making the compounds of formula (I)-(IV).

The disclosure further provides uses of the compounds and compositions of the disclosure as a surfactant, or surface active additive. These compounds and compositions that are used as surfactants demonstrate potential for enhanced performance in personal care formulation applications (e.g., to provide good foam and low skin irritation for shampoo and body wash formulations). Thus, the disclosure also provides a method of using the compounds and the compositions of the disclosure in personal care formulations.

DETAILED DESCRIPTION OF THE INVENTION

In embodiment 4, the disclosure provides compounds of embodiment 1 wherein $R_1$ is hydrogen or $M^+$ (where $M^+$ is a cation forming a salt, such as any base addition salt). In embodiment 5, the disclosure provides compound of embodiment 4, wherein $R_1$ is hydrogen. In embodiment 6, the disclosure provides compound of embodiment 4, wherein $R_1$ is $M^+$. Embodiment 7 provides compounds of embodiment 6, wherein $R_1$ is $Na^+$, or $K^+$.

In embodiment 8, the disclosure provides compounds of embodiment 1 wherein $R_1$ is a polyoxyalkylene moiety having oxyalkyl groups that are the same or different, and where the polyoxyalkylene moiety is capped or uncapped. In embodiment 9, the polyoxyalkylene moiety is polyethylene glycol, methoxypolyethylene glycol, polypropylene glycol, polytetramethylene glycol, or a combination thereof. In embodiment 10, the polyoxyalkylene moiety is polyethylene glycol, methoxypolyethylene glycol, polypropylene glycol, or a combination thereof. Embodiment 11 provides compounds according to any preceding embodiment where the polyoxyalkylene moiety is polyethylene glycol or methoxypolyethylene glycol.

In embodiment 12, the disclosure provides compounds of any one of embodiments 8-11 wherein polyoxyalkylene moiety (e.g., polyethylene glycol or methoxypolyethylene glycol) has a molecular weight between about 80 and about 5000. In embodiment 13, the molecular weight is between about 200 and about 3500. In embodiment 14, the molecular weight is between about 200 and about 1000.

In embodiment 15, the disclosure provides compounds of any one of embodiments 1 or 4-14 wherein $R_2$ is $C_n$ alkyl, and $R_3$ is $C_{n-2}$ alkyl, each optionally substituted with one or more of $R_4$, and wherein n is 4-12. In embodiment 16, the disclosure provides compound of embodiment 15, wherein n is 8-12. In embodiment 17, n is 10. In embodiment 18, the disclosure provides compound of embodiment 15, wherein n is 4-7. In embodiment 19, n is 5.

Embodiment 20 provides compounds according to any one of embodiments 15-19, wherein $R_4$ is halogen, —CN, $C_1$-$C_6$ alkyl, $C_1$-$C_6$ haloalkyl, —NH($C_1$-$C_6$ alkyl), —N($C_1$-$C_6$ alkyl)$_2$, —OH, $C_1$-$C_6$ alkoxy, $C_1$-$C_6$ haloalkoxy, —CO$_2$H, —CO$_2$($C_1$-$C_6$ alkyl), —CON($C_1$-$C_6$ alkyl), or —CON($C_1$-$C_6$ alkyl)$_2$. In embodiment 21, the disclosure provides compound of embodiment 20, wherein $R_4$ is $C_1$-$C_6$ alkyl, $C_1$-$C_6$ haloalkyl, —NH($C_1$-$C_6$ alkyl), —N($C_1$-$C_6$ alkyl)$_2$, —OH, $C_1$-$C_6$ alkoxy, $C_1$-$C_6$ haloalkoxy, or —CO$_2$($C_1$-$C_6$ alkyl).

Embodiment 22 provides compounds according to any one of embodiments 15-19, wherein $R_4$ is $C_1$-$C_6$ alkyl, —OH, $C_1$-$C_6$ alkoxy, —CO$_2$($C_1$-$C_6$ alkyl), or —CON($C_1$-$C_6$ alkyl).

Embodiment 23 provides compounds according to any one of embodiments 15-19, where $R_4$ is aryl, or heteroaryl.

Embodiment 24 provides compounds according to any one of embodiments 15-19, where both $R_2$ and $R_3$ are unsubstituted.

Embodiment 25 provides compounds of embodiment 1 which are:

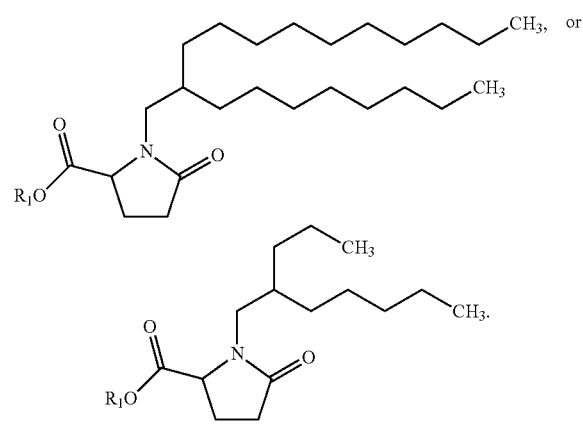

In embodiment 26, the disclosure provides composition of embodiment 2 further comprising at least one additive, excipient or diluent. Embodiment 27 provides compositions of embodiment 2 or 26, wherein each compound is present in about 0.01 to about 100 weight %. In embodiment 28, the composition of embodiment 27 is where at least one compound is present in about >10 weight %. In embodiment 29, the composition of embodiment 28 is where at least one compound is present in about >50 weight %.

In embodiment 30, the disclosure provides composition of any one of embodiments 2 or 26-29 where $R_5$ is hydrogen or $M^+$ (where $M^+$ is a cation forming a salt, such as any base addition salt). In embodiment 31, the disclosure provides composition of embodiment 30, wherein $R_5$ is hydrogen. In embodiment 32, the disclosure provides composition of embodiment 30, wherein $R_5$ is $M^+$. Embodiment 33 provides composition of embodiment 32, wherein $R_5$ is Na$^+$, or K$^+$.

In embodiment 34, the disclosure provides composition of any one of embodiments 2 or 26-29 wherein $R_5$ is a polyoxyalkylene moiety having oxyalkyl groups that are the same or different, and where the polyoxyalkylene moiety is capped or uncapped. In embodiment 35, the polyoxyalkylene moiety is polyethylene glycol, methoxypolyethylene glycol, polypropylene glycol, polytetramethylene glycol, or a combination thereof. In embodiment 36, the polyoxyalkylene moiety is polyethylene glycol, methoxypolyethylene glycol, polypropylene glycol, or a combination thereof. Embodiment 37 provides composition according to any preceding embodiment where the polyoxyalkylene moiety is polyethylene glycol or methoxypolyethylene glycol.

In embodiment 38, the disclosure provides compositions of any one of embodiments 34-37 wherein polyoxyalkylene moiety (e.g., polyethylene glycol or methoxypolyethylene glycol) has a molecular weight between about 80 and about 5000. In embodiment 39, the molecular weight is between about 200 and about 3500. In embodiment 40, the molecular weight is between about 200 and about 1000.

In embodiment 41, the disclosure provides composition of any one of embodiments 2 or 26-40 where $R_6$ is unbranched or branched $C_2$-$C_{24}$ alkyl, or unbranched or branched $C_2$-$C_{24}$ alkenyl, each optionally substituted with one or more of $R_7$. In embodiment 42, $R_6$ is unbranched or branched $C_2$-$C_{24}$ alkyl, optionally substituted with one or more of $R_7$.

In embodiment 43, the disclosure provides composition of any one of embodiments 2 or 26-42 where each $R_8$ independently is hydrogen or $M^+$ (where $M^+$ is a cation forming a salt, such as any base addition salt). In embodiment 44, the disclosure provides composition of embodiment 43, wherein each $R_8$ is hydrogen. In embodiment 45, the disclosure provides composition of embodiment 43, wherein each $R_8$ is $M^+$. Embodiment 46 provides composition of embodiment 45, wherein each $R_8$ is Na$^+$, or K$^+$.

In embodiment 47, the disclosure provides composition of any one of embodiments 2 or 26-42 wherein at least one $R_8$ is a polyoxyalkylene moiety having oxyalkyl groups that are the same or different, and where the polyoxyalkylene moiety is capped or uncapped. In embodiment 48, the polyoxyalkylene moiety is polyethylene glycol, methoxypolyethylene glycol, polypropylene glycol, polytetramethylene glycol, or a combination thereof. In embodiment 49, the polyoxyalkylene moiety is polyethylene glycol, methoxypolyethylene glycol, polypropylene glycol, or a combination thereof. Embodiment 50 provides composition according to any preceding embodiment where the polyoxyalkylene moiety is polyethylene glycol or methoxypolyethylene glycol.

In embodiment 51, the disclosure provides compositions of any one of embodiments 49-50 wherein polyoxyalkylene moiety (e.g., polyethylene glycol or methoxypolyethylene glycol) has a molecular weight between about 80 and about 5000. In embodiment 52, the molecular weight is between about 200 and about 3500. In embodiment 53, the molecular weight is between about 200 and about 1000.

In embodiment 54, the disclosure provides composition of any one of embodiments 2 or 26-53 where $R_9$ is unbranched or branched $C_2$-$C_{24}$ alkyl, or unbranched or branched $C_2$-$C_{24}$ alkenyl, each optionally substituted with one or more of $R_{10}$. In embodiment 55, $R_9$ is unbranched or branched $C_2$-$C_{24}$ alkyl, optionally substituted with one or more of $R_{10}$.

Embodiment 56 provides compositions according to embodiment 2 or 26 comprising at least two compounds of formula (II). In embodiment 57, the composition of embodiment 56 comprises at least two compounds that are:

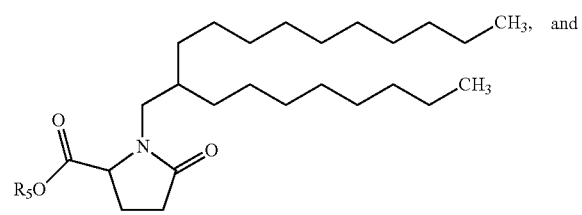

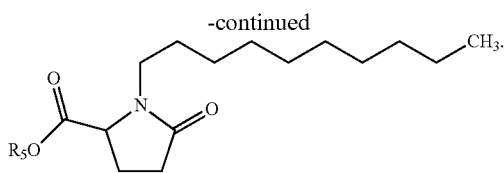

Embodiment 58 provides compositions according to embodiment 56 or 57 further comprising additional compounds according to formula (II) or (III).

Depending on the method of production, unique composition of compound of formula (II) and a compound of formula (III) can be produced. Thus, embodiment 59 provides compositions according to embodiment 2 or 26 comprising at least one compound of formula (II) and one compound of formula (III). In embodiment 60, the composition of embodiment 59 comprises at least two compounds that are:

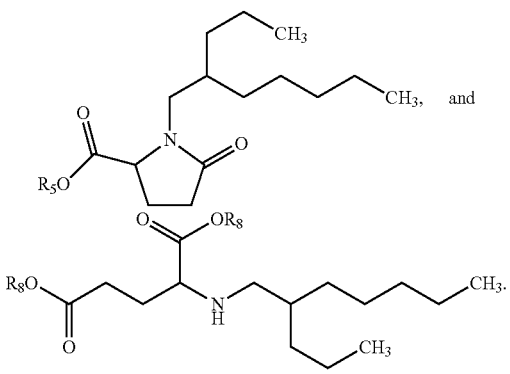

Embodiment 61 provides compositions according to embodiment 59 or 60 further comprising additional compounds according to formula (II) or (III).

The disclosure also provides a compound according to any one of embodiments 1 or 4-25 or a composition according to any one of embodiment 2 or 26-61 for use as a surfactant, or surface active additive. (Embodiment 62)

The disclosure also provides a compound according to any one of embodiments 1 or 4-25 or a composition according to any one of embodiment 2 or 26-61 for use in personal care (shampoo and body wash) formulations, oil recovery, agricultural adjuvants, pesticide inerts, pharmaceutical inerts, textile processing, emulsion polymerization, polymer processing, paint additives, household and institutional cleaning. (Embodiment 63)

In embodiment 64, the disclosure provides methods of embodiment 3 wherein treating the glutamate with the aldehyde is in the presence of base. Embodiment 65 provides methods of embodiment 64 where the base is di($C_1$-$C_6$ alkyl)amine, tri($C_1$-$C_6$ alkyl)amine, tri(hydroxy $C_1$-$C_6$ alkyl)amine, tetra($C_1$-$C_6$ alkyl)guanidine, quinuclidine, pyridine, imidazole, or alkylimidazole. In embodiment 66, the base is triethylamine.

Embodiment 67 provides methods of embodiment 64 where the base is an inorganic base. In embodiment 68, the method of embodiment 67 is where the inorganic base is sodium carbonate.

Embodiment 69 provides method according to any one of embodiments 3 or 64-68 wherein treating the glutamate with the aldehyde is at temperature between about 0 to about 30° C. In embodiment 70, temperature is between about 5 to about 20° C. In embodiment 71, temperature is about 5 to about 10° C.

Embodiment 72 provides method according to any one of embodiments 3 or 64-71 wherein treating the glutamate with the aldehyde is done up to 2 hours.

In embodiment 73, the disclosure provides methods according to any one of embodiments 3 or 64-72 where treating the glutamate with the aldehyde is in the presence of a catalyst and hydrogen gas. Embodiment 74 provides methods of embodiment 73 where the catalyst is a palladium catalyst. For example the palladium catalyst is Pd/C. Embodiment 75 provides methods of embodiment 73 where the catalyst is Raney nickel. Other suitable catalysts include rhodium, platinum, and ruthenium catalysts.

In embodiment 76, the disclosure provides methods according to any one of embodiments 3 or 73-75 wherein treating the glutamate with the aldehyde is in the presence of the catalyst and the hydrogen gas is at temperature between about 10 to about 30° C. In embodiment 77, the temperature is about 20° C.

Embodiment 78 provides methods of embodiment 76 or 77 where treating is at pressure of about 450 psi to about 650 psi.

In embodiment 79, the disclosure provides methods according to any one of embodiments 3 or 64-78 optionally comprising a heating step after treating the glutamate with the aldehyde is in the presence of the catalyst and the hydrogen gas. In embodiment 80, the heating step is at temperature between about 50 to about 120° C. In embodiment 81, the heating step is at temperature about 90° C. In embodiment 82, the heating step is at pressure of about 500 psi to about 800 psi.

Embodiment 83 provides methods according to embodiment 79, wherein the heating step is at temperatures below 90° C. Such embodiment might provide the compositions of embodiment 59 or 60.

Embodiment 84 provides methods according to any one of embodiments 3 or 64-83, wherein treating the glutamate with the aldehyde is in the presence of solvent or mixture of solvents. Suitable solvents include, but are not limited to, water, alcohols, glycols, organic protic solvents, organic aprotic solvents, or mixture thereof. In embodiment 85, the solvent is water, alcohol, or glycol, or mixture thereof. Embodiment 86 provides methods where the solvent is methanol, ethanol, propanol, isopropanol, or butanol, or mixture thereof. In embodiment 87, the solvent is methanol, ethanol, or mixture thereof.

In embodiment 88, the disclosure provides methods according to any one of embodiments 3 or 64-87 wherein $R_{13}$ is $C_1$-$C_{23}$ alkyl or $C_2$-$C_{23}$ alkenyl, each optionally substituted with one or more of $R_{15}$. In embodiment 89, the disclosure provides methods of embodiment 88 wherein $R_{13}$ is $C_4$-$C_{16}$ alkyl optionally substituted with one or more of $R_{15}$. In embodiment 90, the disclosure provides methods of embodiment 88 wherein $R_{13}$ is nonyl optionally substituted with one or more of $R_{15}$. Thus, embodiment 90 provides aldehyde which is decanal. In embodiment 91, the disclosure provides methods of embodiment 88 wherein $R_{13}$ is $C_4$-$C_{16}$ alkenyl optionally substituted with one or more of $R_{15}$. Embodiment 92 provides aldehyde which is 2-propyl-2-heptenal, geranial, or citral.

Embodiment 93 provides methods according to any one of embodiments 3 or 64-87, wherein at least a portion of the aldehyde is the product of in-situ aldol condensation between two aldehydes, which may be the same or different. Such embodiment might also provide the compositions of embodiment 56 or 57. In embodiment 94, when in-situ aldol condensation is performed in the presence of the glutamate, the method provides a mixture of two or more compounds of formula (IV). In embodiment 95, the disclosure provides a method according to according to any one of embodiments 3 or 64-94, wherein one compound of formula (IV) has $R_{12}$ that is branched $C_3$-$C_{24}$ alkyl, branched $C_4$-$C_{24}$ alkenyl, or branched $C_4$-$C_{24}$ alkynyl, each optionally substituted with one or more of $R_{15}$.

Embodiment 96 provides methods according to embodiment 93, wherein the aldehyde is the product of complete in-situ aldol condensation (>90% conversion) between two aldehydes, which may be the same or different, and that at least one of them is enolizable. Suitable aldehydes prepared from this embodiment include but are not limited to α,β-unsaturated aldehydes (for example, 2-propyl-2-heptenal.)

Embodiment 97 provides methods according to any one of embodiments 3 or 64-87, wherein at least a portion of the aldehyde is derived from any functionalization of olefins, before treating the glutamate with the aldehyde. Functionalization method includes, but not limited to, hydroformylation of olefins. Olefins can be alkenes that are mono-, di-, or tri-substituted with $R_{15}$, or conjugated diene with any degree of substitution. Examples of olefins suitable for functionalization include, but not limited to, 1-octene, 4-octene, 2-methyl-propene, myrcene, and farnesene.

Embodiment 98 provides methods according to any one of embodiments 3 or 64-87, wherein the aldehyde can be naturally-derived, petrochemically-derived, or in-situ generated. Non-limiting examples of naturally-derived aldehydes include 3-ethyl-7,11-dimethyldodecanal, geranial, 1-nonanal, and decanal. Non-limiting example of petrochemically-derived aldehyde includes 2-propyl-2-heptenal. Example of in-situ generated aldehyde during the reaction with glutamic acid includes, but not limited to, 2-octyl-dodecanal generated in situ from an aldol condensation of decanal.

Embodiment 99 provides methods according to any one of embodiments 3 or 64-98, wherein only one compound of formula (IV) is prepared.

Embodiment 100 provides methods according to any one of embodiments 3 or 64-98, wherein a mixture of two compounds of formula (IV) is prepared. In embodiment 101, the method according to embodiment 100 provides a mixture wherein one compound has $R_{12}$ that is unbranched $C_3$-$C_{24}$ alkyl, and other compound has $R_{12}$ that is branched $C_3$-$C_{24}$ alkyl.

Embodiment 102 provides methods according to any one of embodiments 3 or 64-101, wherein the method also produces a compound of formula (IV) or a mixture of one or more compounds of formula (IV) and a compound of formula (III).

Compositions and Dosage

In another aspect, the present disclosure provides compositions comprising one or more compounds with respect to formulae (I)-(IV) and an additive, excipient or diluent. The exact nature of the additive, excipient or diluent will depend upon the desired use for the composition. Examples, include, but are not limited to: other cleaning agents (e.g. surfactants, co-surfactants), chelating agents, pH control agents, enzymes, alkalinity sources, thickeners, soil release polymers, defoamers, dispersant polymers, hydrotropes, antibacterial actives, agents, bleaching agents, aesthetic enhancing agents (i.e., dyes, colorants, pigments, perfumes, etc.), oils, solvents, binders, fillers, carrier mediums, pharmaceutically active compounds (e.g., antiviral agents, antitumor agents, antihistamine agents, gene therapy agents, etc.), agrochemically active compounds (e.g., glyphosate, dicamba, 2-4-dichloroacetic acid, etc.), and mixtures thereof.

In particular, the present disclosure provides shampoo and bodywash formulation compositions comprising one or more compounds with respect to formulae (I)-(IV), and one or more of: an anionic (amphoteric, or nonionic surfactant. Anionic surfactants include, but are not limited to sulfates, sulphonates, sulphosuccinates, Isethionates, taurates, etc. Amphoteric surfactants include, but are not limited to betaine, amphoacetate, etc. Nonionic surfactants include, but are not limited to alcohol ethoxylates, amine oxide, etc.

Suitable surfactants are described in Handbook of Surfactants published by Blackie Academic & Professional. The compositions of the disclosure may also comprise: rheology modifiers such as ASE (alkali-soluble emulsion), HASE (Hydrophobically modified alkali-soluble emulsion). HEC (Hydroxyethyl Cellulose), HPMC (Hydroxypropyl methyl cellulose), MC (methyl cellulose), CMC (carboxy methyl cellulose), starch, clay, or other natural polymers. Acrylic rheology modifiers include, but are not limited to, Acrylates/Steareth-20 Methacrylate Copolymer, Acrylates/Beheneth-25 Methacrylate Copolymer, Acrylates Copolymer, PEG-150/Decyl Alcohol/SMDI Copolymer, PEG-150/Stearyl Alcohol/SMDI Copolymer, PEG-150/Distearate, Acrylates/Steareth-20 Methacrylate Crosspolymer, Acrylates/Vinyl Neodecanoate Crosspolymer, and xanthan gum.

The composition may optionally include one or more additional compounds.

The compound(s) described herein, or compositions thereof, will generally be used in an amount effective to achieve the intended result. Dosage amounts will typically be in the range of from about 0.01 to about 100 weight %, or about 1 to about 99 weight %, but may be higher or lower, depending upon, among other factors, the activity as a surfactant, if the material is used as the main active surfactant and various other factors. Skilled artisans will be able to optimize effective dosages without undue experimentation.

A composition of the disclosure may be used in any suitable product form. Suitable product forms include, but not limited to: solids, granules, powders, liquids, gels, pastes, semi-solids, tablets, water-soluble pouches, and combinations thereof. The composition may also be packaged in any suitable form, for example, in a kit.

Definitions

The following terms and expressions used have the indicated meanings.

Terms used herein may be preceded and/or followed by a single dash, "—", or a double dash, "═", to indicate the bond order of the bond between the named substituent and its parent moiety; a single dash indicates a single bond and a double dash indicates a double bond. " $=\!=\!=$ " means a single or double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The term "alkenyl" as used herein, means a straight or branched chain hydrocarbon containing from 2 to 20 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl, and 2-propyl-2-heptenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 20 carbon atoms unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkynyl" as used herein, means a straight or branched chain hydrocarbon group containing from 2 to 10 carbon atoms unless otherwise specified, and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring.

An "aralkyl" or "arylalkyl" group comprises an aryl group covalently attached to an alkyl group, either of which independently is optionally substituted. Preferably, the aralkyl group is aryl($C_1$-$C_6$)alkyl, including, without limitation, benzyl, phenethyl, and naphthylmethyl.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane.

The term "halogen" as used herein, means —Cl, —Br, —I or —F.

The terms "haloalkyl", "haloalkenyl" and "haloalkoxy" refer to an alkyl, alkenyl or alkoxy group, as the case may be, which is substituted with one or more halogen atoms.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. Representative examples of heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, triazinyl, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, or purinyl.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The bicyclic heterocycle is a monocyclic heterocycle fused to either a phenyl, a monocyclic cycloalkyl, a monocyclic cycloalkenyl, a monocyclic heterocycle, or a monocyclic heteroaryl. Representative examples of heterocycle include, but are not limited to, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, trithianyl, 2,3-dihydrobenzofuran-2-yl, and indolinyl.

The phrase "one or more" substituents, as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different. As used herein, the term "independently selected" means that the same or different values may be selected for multiple instances of a given variable in a single compound.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term, unless stated otherwise.

The term "polyoxyalkylene" refers to polymer moieties formed by polymerizing or copolymerizing same or different alkylene oxide monomers to provide polymer moieties of desired size and weight, and the polymer moieties can be capped or uncapped. The polymer can be block or random polymer, or both. In general, the alkylene oxide monomers are independently straight or branched chain groups having from 1-8, preferably 2-5, carbon atoms. Where the polymer moiety comprises two or more polyoxyalkylene groups, the individual polyoxyalkylene groups may be connected to each other by linker groups. Examples of suitable linker groups are: —C(O)—, —O—, —O—C(O)O—, —C(O)$CH_2CH_2$C(O)—, —S—S—, and —$NR^3$—, where $R^3$ is hydrogen, or $C_1$-$C_6$ alkyl. Non-limiting examples of polyoxyalkylene groups include polyoxyethylene, a straight or branched chain polyoxypropylene, and a straight or branched chain polyoxybutylene. Polyoxyalkylene polymer moieties may have molecular weights of from about 80-10,000 Da; any of these moieties may be formed from several shorter, independently-sized units. The units may have molecular weights independently ranging from about 50 (i.e., one repeating unit of a polyethylene glycol), 80, 200, or 500 Da up to about 3000, 4000 or 5000 Da.

"Salt" refers to both acid and base addition salts. Non-limiting examples of acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, lactic acid, oxalic acid, maleic acid, malonic acid, succinic acid, and the like. Non-limiting examples of base addition salts include those formed when an acidic proton present in the parent compound is replaced by a metal ion, such as sodium, potassium, lithium, ammonium, calcium, magnesium, iron, zinc, copper, manganese, aluminum salts, and the like. Salts derived from organic bases include, but are not limited to, salts of primary, secondary, and tertiary amines, substituted amines including naturally occurring substituted amines, cyclic amines and basic ion exchange resins. Examples of organic bases include triethylamine, ethanolamine, triethanolamine, guanidine, and choline.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

Methods of Preparation

The compounds of the present disclosure may be prepared by use of known chemical reactions and procedures. Representative procedures for the preparation of compounds of the disclosure are outlined below in following schemes. It is understood that the nature of the substituents required for the desired target compound often determines the preferred method of synthesis. All variable groups of these methods are as described in the generic description if they are not specifically defined below.

Unless otherwise indicated, $R_{11}$, $R_{12}$, $R_{13}$, and $R_{14}$, and carry the definitions given in connection with formula (IV).

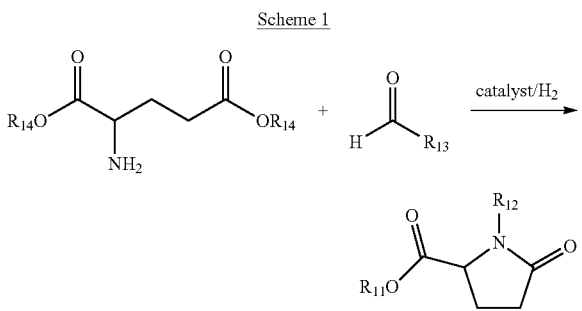

Scheme 1

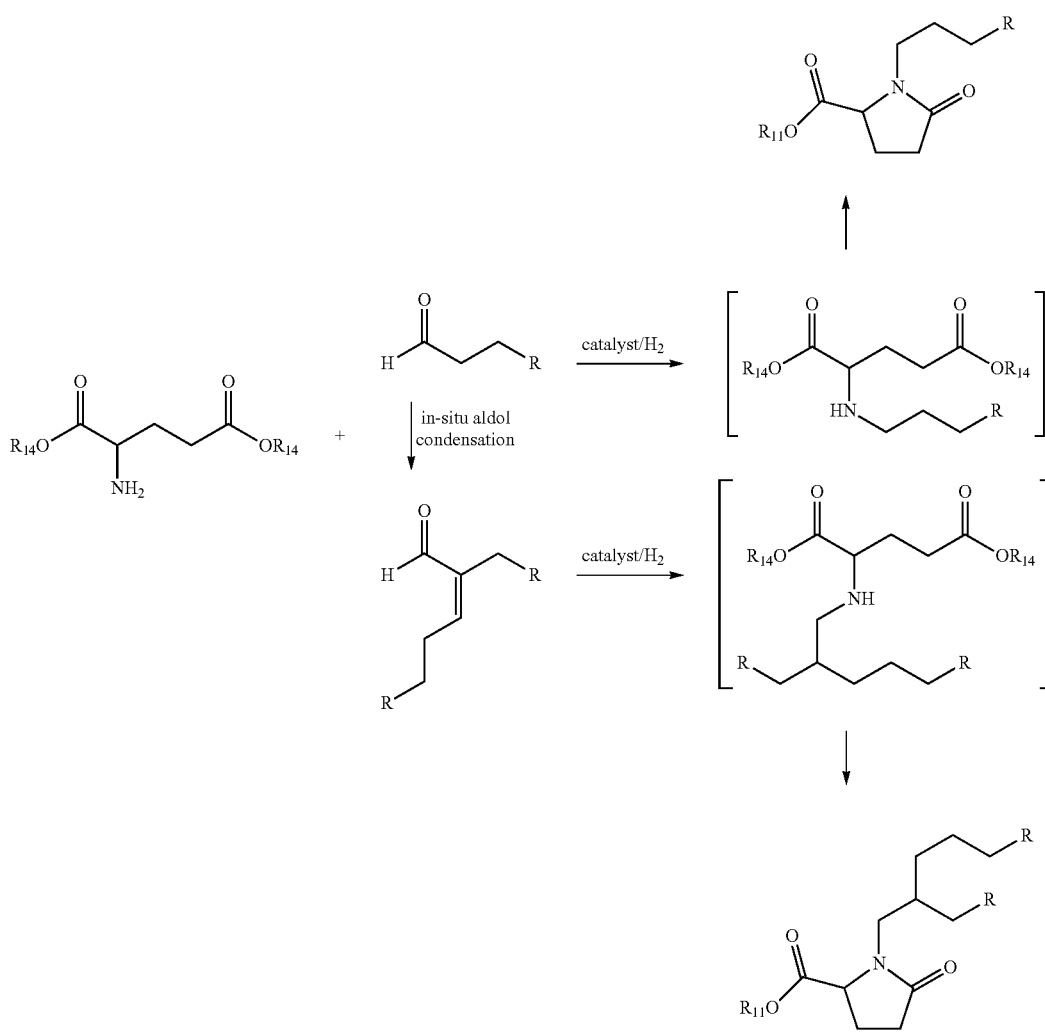

Scheme 2

R is $C_4$—$C_{24}$ alkyl, $C_5$—$C_{24}$ alkenyl, or $C_5$—$C_{24}$ alkynyl, each optionally substituted with one or more of $R_{15}$ Those having skill in the art will recognize that the starting materials and reaction conditions may be varied, the sequence of the reactions altered, and additional steps employed to produce compounds encompassed by the present disclosure, as demonstrated by the following examples.

Starting materials can be obtained from commercial sources including renewable sources, or prepared by well-established literature methods known to those of ordinary skill in the art. The reactions are performed in a solvent appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the disclosure. In some cases, protection of certain reactive functionalities may be necessary to achieve some of the above transformations. In general, the need for such protecting groups as well as the conditions necessary to attach and remove such groups will be apparent to those skilled in the art of organic synthesis.

The disclosures of all articles and references mentioned in this application, including patents, are incorporated herein by reference in their entirety.

EXAMPLES

The preparation of the compounds of the disclosure is illustrated further by the following examples, which are not to be construed as limiting the disclosure in scope or spirit to the specific procedures and compounds described in them.

Equipment and Materials

An Autoclave Engineers 300 mL EZE-SEAL Reactor (Hast C) equipped with electric jacketed heating is used with a 2-225 Kalrez 6375 O-ring gasket. A Control Tower operates the MagnaDrive stirring and controls water cooling through an internal cooling loop via a water solenoid valve. NMR spectra are acquired on a Bruker 400 MHz NMR system. Ultra high purity $H_2$ was supplied in cylinders by Michigan Airgas. The 5% Pd/Carbon Catalyst, 58.07% $H_2O$, is supplied by Johnson Matthey.

Example 1

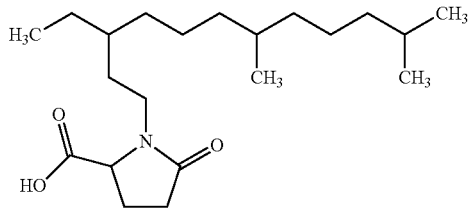 [SMILES: CCC(CCCC(C)CCCC(C)C)CCN1C(=O)CCC1C(=O)O]

Glutamic acid (3.7 g, 0.0251 mol), EtOH (10.5 g), and triethylamine (2.5 g, 0.0247 mol) are added to a clean 100 mL, 3-neck round bottom flask equipped with a magnetic stir bar, a $N_2$ bubbler, addition funnel, thermocouple, and an ice bath. The solution is maintained below 5° C. Farnesene aldehyde (5.0 g, 0.0213 mol) is loaded to the addition funnel and added to the solution with good agitation while keeping the internal temperature below 10° C. 5% Pd/C catalyst (1.204 g, water wet) is weighed and transferred into the 300 mL Autoclave reactor followed by washing the premix solution into the reactor with EtOH (59.2 g). The reactor is sealed and purged with $N_2$ three times at approximately 100 psi with stirring, followed by a pressure check. The reactor is quickly heated to 20° C. with stirring (813 rpm). $H_2$ is charged to the reactor, and pressure is set at approximately 561 psi. The reaction is carried out for approximately 19 hours 57 minutes. The pressure is released and a reaction sample (~2 mL) is withdrawn via syringe using the reactor sample port. The sample is filtered using a 0.45 μm Polypropylene syringe filter (Whatman International, Ltd., Maidstone, England) and analyzed by NMR. The analysis determined the transformation to the open-chain N-alkyl glutamic acid derivative is nearly complete.

The reactor is then purged with 100 psi $N_2$ three times with stirring. The reactor is quickly heated to 90° C. with stirring (813 rpm). $H_2$ is charged to the reactor, and pressure is set at approximately 751 psi. The reaction is carried out for approximately 21 hrs 23 minutes. The system is cooled and $H_2$ vented. A reaction sample (~2 mL) is withdrawn as previously described, filtered using a 0.45 μm Polypropylene syringe filter, and analyzed by NMR. The analysis determined the transformation to the pyroglutamate is sufficiently complete. The reaction mixture is discharged from the reactor, and filtered using a 30 mL glass medium fritted funnel and a celite bed. A small amount of glutamic acid-like crystals are observed in the bottom of the reactor vessel while transferring the material to the filtercake. The bed is washed with an additional 23 mL EtOH. Material (clear appearance) is transferred to a 250 mL round bottom flask for further work-up.

The filtrate is then concentrated to a thick oil on the rotary evaporator (bath temperature 45° C.). This is swirled in 50 mL of hexanes, dissolving a majority of the oil. About 5 mL of pH 6.5, 1M phosphate buffer solution is added. This resulted in two phases, the largest is on the bottom. The bottom phase is drained off through a layer of filter aid in a coarse sintered glass funnel, with vacuum applied to the filter flask, to remove some suspended crystalline solids. The top phase (5-10 mL) is drained into a round bottom flask and concentrated to dryness, giving about 1 g of a thick, tan oil. TLC (silica gel, 2 vol % 28% $NH_3$ in water/98 vol % EtOH, $I_2$ visualization) indicated a material with an $R_f$ of about 0.85.

A small amount of hexanes is added back to the filtrate and the solution is returned to the separatory funnel. The mixture is diluted with 50 mL of a 50/50 mix of MeOH and water. Two phases formed, the upper, primarily hexane. TLC of both phases showed that more of the material had been extracted into the hexane phase. An additional extraction of the MeOH/water phase is performed using 10 mL of hexanes. The combined hexanes phases are concentrated on the rotary evaporator (Bath T=45° C.) to give approximately 1.5 g of a thick, light amber oil.

The lower, MeOH/water phase, is adjusted to pH 5 by addition of several mL of 1M HCl. A pale viscous pink oil separates as a more dense phase. To the mixture is added 20 mL of $CH_2Cl_2$, the mixture is shaken briefly, and then allowed to settle a few minutes. The $CH_2Cl_2$ phase is drawn off and then concentrated to a viscous oil on the rotary evaporator (bath temperature is 45° C.). The NMR spectra of a sample indicated that there are two or more components. The material is then placed under full pump vacuum (5 mmHg) for several hours (yield, 4.40 g). A small sample is submitted for mass spectral characterization. The major component by LC/MS has an exact mass of 353.2930, $C_{21}H_{39}NO_3$. TLC of the remaining aqueous phase did not reveal any significant amounts of additional components. $^1$H NMR (400 MHz, $CDCl_3$) δ 8.9 (br s, 1H), 4.21 (dd, J=9.0, 3.1 Hz, 1H), 3.85-3.56 (m, 1H), 2.965-2.85 (m, 1H), 2.6-2.08 (m, 4H), 1.72-1.42 (m, 3H), 1.4-1.0 (m, 16H), 0.95-0.75 (m, 12H). $^{13}$C NMR (100.6 MHz, $^1$H-decoupled, $CDCl_3$) δ 176.04, 174.86, 174.83, 59.89, 59.77, 40.05, 39.35, 37.47, 37.38, 37.34, 36.91, 36.74, 33.46, 33.21, 32.76, 30.35, 29.79, 27.96, 25.67, 25.59, 25.38, 25.29, 24.79, 24.78, 24.48, 24.11, 23.97, 23.20, 22.71, 22.61, 19.67, 19.65, 10.73, 10.69, 10.48, 10.43.

Example 2

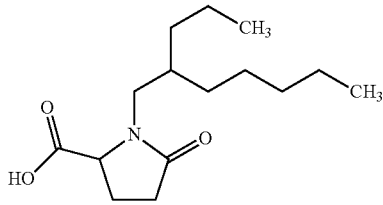 [SMILES: CCCCCC(CCC)CN1C(=O)CCC1C(=O)O]

Glutamic acid (9.51 g, 0.0646 mol), MeOH (20.6 g), and triethylamine (13.1 g, 0.130 mol) are added to a clean 250 mL, 3-neck round bottom flask equipped with a magnetic stir bar, a $N_2$ bubbler, addition funnel, thermocouple and an ice bath. The solution is maintained below 5° C. 2-Propylhept-2-enal (10.0 g, 0.0648 mol) is loaded to the addition funnel and added to the solution with good agitation while keeping the internal temperature below 10° C. 5% Pd/C catalyst (2.084 g, water wet as described in the general experimental) is weighed and transferred into the 300 mL Autoclave reactor followed by washing the premix solution into the reactor with MeOH (106.0 g). The reactor is sealed and purged with $N_2$ three times at approximately 100 psi with stirring, followed by a pressure check. The reactor is quickly heated to 20° C. with stirring (806 rpm). $H_2$ is charged to the reactor, and pressure is set at approximately 586 psi. The reaction is carried out for approximately 4 hrs 50 minutes. A reaction sample (~2 mL) is extracted using the reactor sample port, filtered using a 0.45 μm Polypropylene syringe filter and analyzed by NMR, which shows a mixture of linear and cyclized structures. The reactor is purged with 100 psi $N_2$ three times with stirring. The reaction is then continued at an elevated temperature and pressure. The reactor is quickly heated to 90° C. with stirring (806 rpm). $H_2$ is charged to the reactor, and pressure is set at approximately 809 psi. The reaction is carried out for approximately 18 hours 41 minutes. The system is cooled and $H_2$ vented. A reaction sample (~2 mL) is extracted using the reactor sample port, filtered using a 0.45 μm Polypropylene syringe filter and analyzed by NMR. The analysis determined the transformation to the pyroglutamate is essentially complete. The reaction mixture is discharged from the reactor, and filtered using a 60 mL glass medium fritted funnel and a celite bed. The bed is washed with an additional 10 mL MeOH. Material (clear, non-colored appearance) is transferred to a 250 mL round bottom flask for further work-up.

The filtrate is concentrated to a thick oil on the rotary evaporator (bath temperature 45° C.) and then put on the vacuum pump overnight to give 13.2 g of a faint pink oil. This is dissolved in 50 mL of MeOH. 50 mL of de-ionized water containing 2.0 g (0.05 mol) of sodium hydroxide pellets is added and the solution is transferred to a 125 mL separatory funnel and extracted with 3×20 mL of hexanes. The aqueous MeOH phase is then acidified (pH<3) with 5.0 g of 37% HCl. Two phases formed. To the mixture is added 20 mL of $CH_2Cl_2$, the mixture is shaken briefly, and then allowed to settle a few minutes. The $CH_2Cl_2$ phase is drawn off and the aqueous MeOH is extracted with additional $CH_2Cl_2$ (2×20 mL). The $CH_2Cl_2$ extracts are combined and concentrated to a viscous oil on the rotary evaporator (bath temperature is 45° C.). The pale violet oil is placed under full pump vacuum overnight with gentle warming (30-40° C.) and stirring. The oil crystallized (11.0 g). NMRs ($^{13}$C- & $^1$H-) showed that the material is substantially free of triethylamine. $^1$H NMR (400 MHz, CDCl$_3$) δ 10.76 (br s, 1H), 4.21 (ddd, J=9.1, 2.5, 1.0 Hz, 1H), 3.67 (ddd, J=13.9, 9.4, 2.0 Hz, 1H), 2.84 (ddd, J=14.0, 5.1, 2.5 Hz, 1H), 2.65-2.24 (m, 3H), 2.18 (ddt, J=12.8, 9.3, 3.1 Hz, 1H), 1.70-1.56 (m, 1H), 1.42-1.1 (m, 12H), 0.92-0.82 (m, 6H). $^{13}$C NMR (100.6 MHz, $^1$H-decoupled, CDCl$_3$) δ 176.99, 174.54, 60.00, 45.99, 35.32, 33.92, 33.59, 32.18, 31.60, 31.25, 29.60, 26.13, 25.73, 23.14, 22.57, 19.69, 19.23, 14.42, 14.36, 14.04.

Example 3

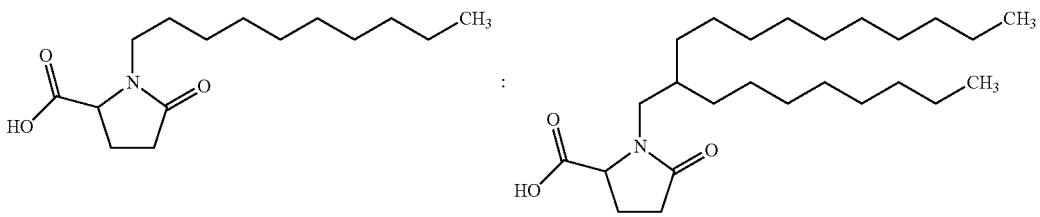

(35:65 weight ratio)

Glutamic acid (10.0 g, 0.068 mol), MeOH (20.7 g), and triethylamine (12.95 g, 0.128 mol) are added to a clean 250 mL, 3-neck round bottom flask equipped with a magnetic stir bar, a $N_2$ bubbler, addition funnel, thermocouple and an ice bath. The solution is maintained below 5° C. Decanal (10.1 g, 0.0646 mol) is loaded to the addition funnel and added to the solution with good agitation while keeping the internal temperature below 10° C. The mixture at this stage had a slight yellow appearance. 5% Pd/C catalyst (2.008 g, water wet) is weighed and transferred into the 300 mL Autoclave reactor followed by washing the premix solution into the reactor with MeOH (105.8 g). The reactor is sealed and purged with $N_2$ three times at approximately 100 psi with stirring, followed by a pressure check. The reactor is quickly heated to 20° C. with stirring (807 rpm). $H_2$ is charged to the reactor, and pressure is set at approximately 551 psi. The reaction is carried out for approximately 5 hrs 32 minutes. A reaction sample (~2 mL) is extracted using the reactor sample port, filtered using a 0.45 μm Polypropylene syringe filter and analyzed by NMR. The analysis determined the transformation to the open chain N-alkylglutamic acid is nearly complete and the reaction is continued at an elevated temperature and pressure. NMR spectral data on a sample of the open-chain glutamic acid derivative: $^1$H NMR (400 MHz, CDCl$_3$) δ 4.75 (br s, 3H), 3.4 (m, 1H), 2.8 (m, 2H), 2.55-2.3 (m, 2H), 2.15-2.0 (m, 2H), 1.75-1.6 (m, 1H), 1.5-1.1 (br m, 23H), 0.95-0.70 (m, 4.5H). $^{13}$C NMR (100.6 MHz, $^1$H decoupled, CDCl$_3$) δ 179.60, 172.56, 51.85, 45.84, 36.29, 35.44, 31.87, 31.84, 31.31, 31.24, 29.84, 29.61, 29.58, 29.52, 29.30, 29.26, 26.36, 26.20, 22.64, 22.62, 14.05.

The reactor is purged with 100 psi N₂ three times with stirring. The reactor is quickly heated to 90° C. with stirring (807 rpm). H₂ is charged to the reactor, and pressure is set at approximately 702 psi. The reaction is carried out for approximately 18 hrs 41 minutes. The system is cooled and H₂ vented. A reaction sample (~2 mL) is extracted using the reactor sample port, filtered using a 0.45 μm Polypropylene syringe filter and analyzed by NMR. The analysis determined the transformation to the N-alkylpyroglutamic acid is effectively complete. The reaction mixture is discharged from the reactor, and filtered using a 60 mL glass medium fritted funnel and a celite bed. The bed is washed with an additional 10 mL MeOH. Material (clear, non-colored appearance) is transferred to a 250 mL round bottom flask for further work-up.

The filtrate is concentrated to a thick oil (approximately 20 g) on the rotary evaporator (bath temperature 45° C.). This is dissolved in 50 mL of MeOH. A white crystalline precipitate formed, is filtered off, and washed with ~20 mL of MeOH. This is identified as glutamic acid by ¹H-NMR. The MeOH filtrate is then treated with 18 g of 15 wt % sodium hydroxide and 32 g of deionized water. The basic solution is extracted with 20 mL of hexanes in a 125 mL separatory funnel. CH₂Cl₂ (20 mL) is added, resulting in a homogeneous solution. This solution is then extracted with another 20 mL of hexanes. The aqueous MeOH phase is then acidified (pH<3) with 13.25 g of 37% HCl, and two phases formed. The mixture is extracted with 3×20 mL of CH₂Cl₂. The CH₂Cl₂ extracts are combined and concentrated on the rotary evaporator. The thick pink syrup is then placed under full pump vacuum overnight with stirring and heating to about 30-40° C. The weight of product obtained is 11.81 g and the weight of recovered (air dried) glutamic acid is 1.87 g.

¹H-NMR showed that this material still contained significant amounts of triethylamine. It is thus combined with another small batch of crude mixture prepared in a similar manner. These two batches are dissolved with stirring in 50 mL of MeOH. Deionized H₂O (50 mL) containing 2.33 g (0.0583 mol) of sodium hydroxide is added and the solution is stirred at room temperature over the weekend. The solution is poured into a 250 mL separatory funnel and extracted with hexanes (3×20 mL), allowing about 20 min settling time for each extraction. The basic solution is acidified with 5.88 g of 37% HCl to pH<3. The acidified, 2-phase mixture is diluted with 20 mL of CH₂Cl₂. The CH₂Cl₂ product phase is drawn off and the aqueous solution is extracted with additional CH₂Cl₂ (2×20 mL). The combined CH₂Cl₂ extracts are concentrated to a thick oil on the rotary evaporator (bath temperature is 45° C.). and then placed under full pump vacuum overnight with stirring and heating to about 30-40° C. to remove residual solvents. The recovered weight of material is 13.96 g. ¹H- and ¹³C-NMR spectra showed that the material is substantially free of triethylamine (0.2 wt %) and the material is an approximately 43.3:56.7 molar mixture of the C₁₀ and C₂₀ N-alkyl pyroglutamic acids (35:65 wt. ratio). LC/MS m/s [M+H]⁺ 410.36 (exact mass 409.36, C₂₅H₄₇NO₃) and 270.21 (exact mass 269.20, C₁₅H₂₇NO₃). A small amount of the open chain C₂₀ compound is also observed by LC/MS with [MH]+ of 428.3757 (exact mass 427.37, C₂₅H₄₉NO₄).

Example 4

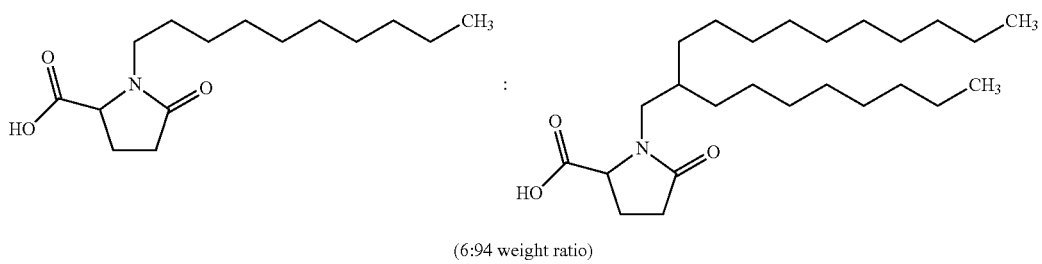 [SMILES: CCCCCCCCCCN1C(=O)CCC1C(=O)O ; ":" ; CCCCCCCCCCC(CCCCCCCC)CN1C(=O)CCC1C(=O)O]

(6:94 weight ratio)

Glutamic acid (10.9 g, 0.0741 mol), MeOH (25.0 g), and triethylamine (15.30 g, 0.1512 mol) are added to a clean 500 mL, 3-neck round bottom flask equipped with a magnetic stir bar, a N₂ bubbler, addition funnel, thermocouple, and an ice bath. The solution is maintained below 5° C. Decanal (17.5 g, 0.112 mol) is loaded to the addition funnel and added to the solution with good agitation while keeping the internal temperature below 10° C. The mixture is stirred for ~1.5 hours. At this stage, the premix had a slight yellow appearance. 5% Pd/C catalyst (2.08 g, water wet) is weighed and transferred into the 300 mL Autoclave reactor followed by washing the premix solution into the reactor with MeOH (91.0 g). The reactor is sealed and purged with N₂ three times at approximately 100 psi with stirring, followed by a pressure check. The reactor is quickly heated to 20° C. with stirring (811 rpm). H₂ is charged to the reactor, and pressure is set at approximately 500 psi. The reaction is carried out for approximately 2 hours 28 minutes. The reactor is vented of H₂ prior to continuing at an elevated temperature and pressure. The reactor is quickly heated to 90° C. with stirring (811 rpm). H₂ is charged to the reactor, and pressure is set at approximately 701 psi. The reaction is carried out for approximately 20 hrs. The system is cooled, H₂ vented and N₂ purged through the reactor before discharging the contents. The reaction mixture is filtered using a 60 mL glass medium fritted funnel and a celite bed. The bed is washed with an additional 20 mL MeOH. Material is observed to have a clear, slightly yellowed appearance. No crystals are observed in the bottom of the reactor when transferring to the filter. Only a small thin ring of white crystal-like material is observed at the solvent stirring level in the reactor. The filtered material is transferred to a 500 mL round bottom flask for further work-up.

The filtrate (144.33 g) is concentrated to a thick oil (approximately 25 g) on the rotary evaporator (bath temperature 45° C.). Upon cooling some white crystalline solids are deposited (glutamic acid). The oily residue is dissolved in 50 mL of MeOH and combined with a second batch of crude material in 50 mL of MeOH prepared in a similar manner. The combined MeOH solutions are diluted with 100 mL of water containing 6.0 g of sodium hydroxide pellets and transferred into a 500 mL separatory funnel. The basic solution is extracted with 100 mL of hexanes and then with 3×50 mL of hexane. About 40 mL of hexane stayed dissolved in the basic aqueous MeOH mixture. The aqueous MeOH phase is then acidified (pH<3) with 15.8 g of 37% HCl. Two phases formed, an upper hexane phase (yellow) containing the N-alkyl pyroglutamic acid and a lower aqueous phase. After separation of the upper phase, the aqueous phase is extracted with 2×50 mL of $CH_2Cl_2$. The $CH_2Cl_2$ extracts are colorless. The warm aqueous MeOH phase is set aside and allowed to cool. A significant amount of white crystals separated (glutamic acid). The $CH_2Cl_2$ extracts are combined with the hexane phase and washed once with about 25 mL of water. After letting the phases separate, the organic phase is concentrated on the rotary evaporator. The thick pale yellow syrup is then placed under full pump vacuum overnight with stirring and heating to about 30-40° C. to remove residual solvents. The weight of product obtained is 33.87 g. $^1$H-NMR analysis showed that it is 92.64 wt % $C_{20}$ N-alkyl pyroglutamic acid, 6.50 wt % $C_{10}$ N-alkyl pyroglutamic acid, 0.84 wt % $Et_3N$, and 0.02 wt % $CH_2Cl_2$. $^1$H NMR (400 MHz, $CDCl_3$) δ 8.78 (br s, 1H), 4.21 (d, J=3.2 Hz, shoulder), 4.17 (dd, J=9.0, 2.5 Hz, 1H), 3.81-3.71 (m, shoulder), 3.66 (dd, J=13.9, 9.5 Hz, 1H), 2.91 (ddd, J=13.8, 8.6, 5.4 Hz, 0.106H), 2.77 (dd, J=13.9, 5.2 Hz, 0.995H), 2.69-2.23 (m, 3H), 2.23-1.99 (m, 1H), 1.62 (s, 1H), 1.55-1.0 (br s, 32H), 0.88 (t, J=6.7 Hz, 6H). $^{13}$C NMR (100.6 MHz, $^1$H-decoupled, $CDCl_3$) δ 176.52, 176.24, 175.25, 60.17, 59.89, 45.94, 45.46, 41.97, 35.58, 31.91, 31.69, 31.18, 30.07, 30.04, 29.68, 29.67, 29.65, 29.61, 29.56, 29.35, 29.33, 29.31, 27.05, 26.95, 26.50, 26.11, 23.25, 22.67, 14.10.

Example 5

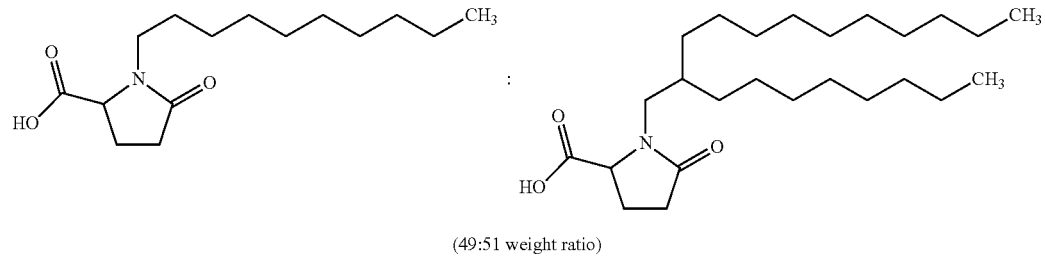 [SMILES: CCCCCCCCCCN1C(=O)CCC1C(=O)O ; ":" ; CCCCCCCCCCC(CCCCCCCC)CN1C(=O)CCC1C(=O)O]

(49:51 weight ratio)

Glutamic acid (10.9 g, 0.0741 mol), MeOH (25.23 g), and triethylamine (16.60 g, 0.1640 mol) are added to a clean 500 mL, 3-neck round bottom flask equipped with a magnetic stir bar, a $N_2$ bubbler, addition funnel, thermocouple and an ice bath. The solution is maintained below 5° C. Decanal (17.5 g, 0.112 mol) is loaded to the addition funnel and added to the solution with good agitation while keeping the internal temperature below 10° C. The mixture is stirred for approximately ~1 hour total, including loading the premix into the reactor and completing the $N_2$ purge step. The reactor vessel bottom is chilled in a bucket of ice. The premix, at the time of transfer, had only a slight yellow creamy appearance. 5% Pd/C catalyst (2.14 g, water wet) is weighed and transferred into the 300 mL Autoclave reactor followed by washing the premix solution into the reactor with MeOH (94.0 g). The reactor is sealed and purged with $N_2$ three times at approximately 100 psi with stirring, followed by a pressure check. The reactor is quickly heated to 20° C. with stirring (806 rpm). $H_2$ is charged to the reactor, and pressure is set at approximately 583 psi. The reaction is carried out for approximately 5 hours 41 minutes. The reactor is vented of $H_2$ prior to continuing at an elevated temperature and pressure. The reactor is quickly heated to 90° C. with stirring (806 rpm). $H_2$ is charged to the reactor, and pressure is set at approximately 726 psi. The reaction is carried out for approximately 24 hours 5 minutes. The system is cooled, $H_2$ vented and $N_2$ purged through the reactor before discharging the contents. The reaction mixture is filtered using a 60 mL glass medium fritted funnel and a celite bed. The bed is washed with an additional 20 mL MeOH. Material is observed to have a clear, slightly yellowed appearance. No crystals are observed in the bottom of the reactor when transferring to the filter. Only a small thin ring of white crystal-like material is observed at the solvent stirring level in the reactor. The filtered material is transferred to a 500 mL round bottom flask for further work-up.

The filtrate (177.3 g) is concentrated to a thick oil (approximately 26 g) on the rotary evaporator (bath temperature 45° C.). Upon cooling, unlike in example 4, the thick, nearly colorless syrup did not deposit any solids. The syrup is dissolved in 50 mL of MeOH then diluted with 50 mL of water containing 3.1 g of sodium hydroxide pellets. The solution is transferred into a 500 mL separatory funnel and extracted with 100 mL of hexanes. This is followed with extractions with 3×50 mL of hexanes. The aqueous MeOH phase is then acidified (pH<3) with 7.9 g of 37% HCl. Two phases formed, an upper hexane phase (pale yellow) containing the N-alkyl pyroglutamic acid and a lower aqueous phase. After separation of the upper phase, the aqueous phase is extracted with 2×25 mL of $CH_2Cl_2$. The $CH_2Cl_2$ extracts are combined with the hexane phase and the combined organics are concentrated on the rotary evaporator. The thick pale yellow syrup (21.75 g) is then placed under full pump vacuum overnight with stirring and heating to about 30-40° C. to remove residual solvents. The weight of product obtained is 20.81 g (85% yield). $^1$H-NMR analysis showed that it is 50.60 wt % $C_{20}$ N-alkyl pyroglutamic acid, 48.74 wt % $C_{10}$ N-alkyl pyroglutamic acid, and 0.65 wt % $Et_3N$. $^1$H NMR (400 MHz, $CDCl_3$) δ 10.61 (br s, 1H), 4.22 (ddd, J=13.4, 9.2, 2.8 Hz, 1H), 3.80-3.63 (m, 1H), 2.95 (ddd, J=14.0, 8.8, 5.4 Hz, 0.63H), 2.81 (dd, J=14.0, 5.3 Hz, 0.44H), 2.65-2.28 (m, 2H), 2.22-2.12 (m, 1H), 1.8-1.4 (m, 2H), 1.25 (br s, 23H), 0.88 (dd, J=7.0, 6.5 Hz, 4.5H). $^{13}$C NMR (100.6 MHz, $^1$H-decoupled, $CDCl_3$) δ 176.81, 176.51, 174.72, 59.96, 59.66, 46.02, 42.13, 35.56, 31.90, 31.87, 31.65, 31.23, 30.01, 29.65, 29.60, 29.52, 29.42, 29.35, 29.28, 26.99, 26.90, 26.48, 26.11, 23.17, 23.11, 22.66, 14.09.

Example 6

Preparation of Larger Batch of $C_{10}/C_{20}$ Pyroglutamic Acid

A large batch of N—$C_{10}/C_{20}$ pyroglutamic acid prepared as described in Example 5 is dissolved in 50 mL of $CH_2Cl_2$ and is filtered through a medium frit glass funnel to remove some insoluble material. The filtrate is concentrated to a thick oil on the rotary evaporator (bath temperature 45° C.). After holding the material (with stirring) overnight at 35° C. under a full pump vacuum to remove residual solvent, the weight of product obtained is 38.78 g. $^1$H-NMR analysis gave the following composition: 47.77 wt % $C_{10}$ N-alkyl pyroglutamic acid, 51.52 wt % $C_{20}$ N-alkyl pyroglutamic acid, 0.57 wt % $Et_3N$, and 0.14 wt % $CH_2Cl_2$.

Example 7

Critical Micelle Concentration

The critical micelle concentration (Kibron CMC) and surface tension of the N-alkyl pyroglutamic acids (as Na$^+$ salts) and related commercial surfactants were evaluated. For each sample, a total of twelve dilutions starting at 1 wt % were prepared, reducing the concentration in each dilution by half by taking an aliquot of the previous dilution and adding the same amount of water. The surface tension of all 12 dilutions was measured using a Kibron Delta-8 multichannel microtensiometer. Sample volume for each analysis was 50 µL. Results were summarized in Table 1.

TABLE 1

| Product of Example No. | Sodium Salt Properties | | |
|---|---|---|---|
| | Kibron CMC (ppm) | Surface Tension (1%) Dynes/cm | Shake Foam t = 0 (mL) |
| 1 | 625 | 38 | 36 |
| 2 | >10000 | 34 | 11 |
| 3 | 78 | 28 | 34 |
| 4 | 78 | 29 | 29 |
| 6 | 78 | 29 | 38 |

All alkyl pyroglutamates in Table 1 can reduce the surface tension of water to 30-40 dynes/cm at 1 wt % solid. This is typical for common anionic surfactants such as sodium laureth sulfate.

Example 8

Foam Height Analysis

Foaming profile of the N-alkyl pyroglutamates are evaluated using a shake foam test, and evaluated against sodium laureth sulfate. For each sample, a 0.1 wt % solution is prepared by diluting 50 mg active to 50 g in water. The 0.1 wt % solution is added to a 100 mL graduated cylinder and capped. The cylinder is shaken by hand 20 times, each time the cylinder is inverted and brought back to an upright position. Foam height (in mL) is defined as the highest point of the top layer of the foam in the graduated cylinder. If the top of the foam was not flat, the midpoint of the top of the foam was reported. Foam height is read immediately after the solution settled (t=0). Three replicates are done for each sample, and the reported foam height (in mL) is the average reading of the three replicates.

Ross Miles foam height data for compound of Example 3 are recorded in Table 2. The foam height trend obtained from the Ross Files foam height test agreed with the simple shake foam tests used in this work, indicating that example 3 is a surfactant that provides stable foam.

TABLE 2

| Product of Example No. | Ross Miles foam (mm) | Dynamic surface tension (dynes/cm) | Contact angle on Teflon (°) |
|---|---|---|---|
| 3 | 0 min: 150<br>5 min: 135 | 71 (4 bubbles/s) | 70 |

Example 9

Water Solubility

Selected N-alkyl pyroglutamic acids are converted into their sodium salt by neutralizing them in water with sodium hydroxide. In general, a known amount of sample is placed in a vial and a known amount of water is added. Sample is neutralized with 25 wt % sodium hydroxide in water until pH is >7. Mild heating (50° C.) is applied when necessary to aid dissolution. The final mass is recorded. The weight percent of the solution is determined by mass of the sodium salt over the total mass of solution, and multiplying by 100. The pH of the solution is recorded after neutralization. The water solubility results are summarized in Table 3. No effort was done to prepare a saturated solution. All the examples tested for water solubility (example 1, 2, 4, 6) in Table 4 have high water good water solubility (>10 wt %).

TABLE 3

| Product of Example No. | Solubility (wt %) | pH |
|---|---|---|
| 1 | 24.3 | 10.0 |
| 2 | 21.4 | 7.3 |
| 4 | 15.4 | 7.1 |
| 6 | 26.9 | 7.0 |

It is understood that the examples and embodiments described herein are for illustrative purposes only. Unless clearly excluded by the context, all embodiments disclosed for one aspect of the invention can be combined with embodiments disclosed for other aspects of the invention, in any suitable combination. It will be apparent to those skilled in the art that various modifications and variations can be made to the present invention without departing from the scope of the invention. Thus, it is intended that the present invention cover the modifications and variations of this invention provided they come within the scope of the appended claims and their equivalents. All publications, patents, and patent applications cited herein are hereby incorporated herein by reference for all purposes.

What is claimed is:

1. A compound of the formula (I):

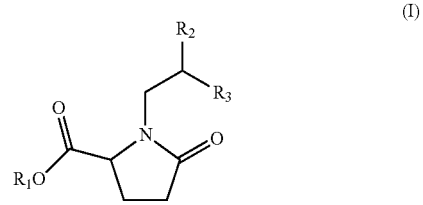

or acceptable salts, hydrates, or solvates thereof; wherein
$R_1$ is hydrogen, $C_1$-$C_6$ alkyl, $C_1$-$C_6$ hydroxyalkyl, M$^+$, or a polyoxyalkylene moiety having oxyalkyl groups that are the same or different, and where the polyoxyalkylene moiety is capped or uncapped;
where M$^+$ is a cation forming a salt;
$R_2$ and $R_3$ are independently $C_2$-$C_{24}$ alkyl, $C_2$-$C_{24}$ alkenyl, or $C_2$-$C_{24}$ alkynyl, each optionally substituted with one or more of $R_4$; and
wherein $R_4$ is halogen, —CN, $C_1$-$C_6$ alkyl, $C_2$-$C_6$ alkenyl, $C_2$-$C_6$ alkynyl, $C_1$-$C_6$ haloalkyl, —NH($C_1$-$C_6$ alkyl), —N($C_1$-$C_6$ alkyl)$_2$, —OH, $C_1$-$C_6$ alkoxy, $C_1$-$C_6$ haloalkoxy, —CO$_2$H, —CO$_2$($C_1$-$C_6$ alkyl), —CON($C_1$-$C_6$ alkyl), —CON($C_1$-$C_6$ alkyl)$_2$, $C_3$-$C_8$ cycloalkyl, aryl, heteroaryl, or heterocyclyl, wherein each cycloalkyl, aryl, heteroaryl, and heterocyclyl are optionally substituted with one or more of halogen, —CN, $C_1$-$C_6$ alkyl, $C_1$-$C_6$ haloalkyl, —NH$_2$, —NH($C_1$-$C_6$ alkyl), —N($C_1$-

$C_6$ alkyl)$_2$, —OH, $C_1$-$C_6$ alkoxy, $C_1$-$C_6$ haloalkoxy, —CO$_2$H, —CO$_2$($C_1$-$C_6$ alkyl), —CON($C_1$-$C_6$ alkyl), or —CON($C_1$-$C_6$ alkyl)$_2$;

or $R_4$ is polyoxyalkylene moiety having oxyalkyl groups that are the same or different, and where the polyoxyalkylene moiety is capped or uncapped.

2. A compound according to claim 1, wherein $R_1$ is hydrogen or M$^+$.

3. A compound according to claim 1, wherein $R_1$ is a polyoxyalkylene moiety having oxyalkyl groups that are the same or different, and where the polyoxyalkylene moiety is capped or uncapped.

4. A compound according to claim 1, wherein $R_2$ is $C_n$ alkyl, and $R_3$ is $C_{n-2}$ alkyl, each optionally substituted with one or more of $R_4$, and wherein n is 4-12.

5. A compound according to claim 4, wherein n is 5 or 10.

6. A compound according to claim 1, which is:

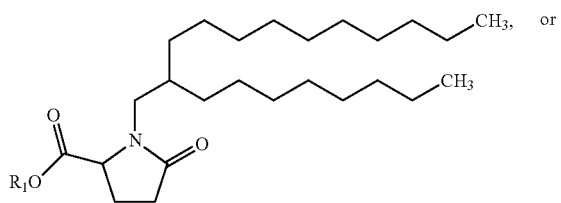 or 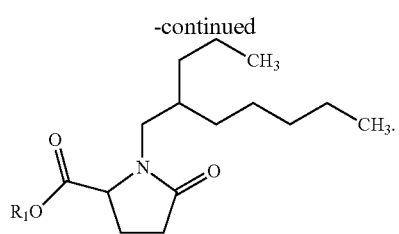

7. A composition comprising a compound according to claim 1, and at least one additive, excipient or diluent.

8. A compound according to claim 1 which is suitable as a surfactant, surface active additive, or phase transfer catalyst.

9. A compound according to claim 1 which is suitable in personal care formulations.

10. A personal care formulation comprising a compound according to claim 1.

11. A personal care formulation comprising a composition according to claim 7.

12. A method for carrying out phase transfer in a reaction system comprising adding to the system a compound according to claim 1.

13. A method for carrying out phase transfer in a reaction system comprising adding to the system a composition according to claim 7.

14. A personal care formulation according to claim 10, where the formulation is a shampoo or a body wash formulation.

* * * * *